United States Patent [19]
Brown et al.

[11] Patent Number: 5,127,258

[45] Date of Patent: Jul. 7, 1992

[54] DUPLEX SAMPLING APPARATUS AND METHOD

[75] Inventors: Paul E. Brown, Pittsburgh; Robert Lloyd, West Mifflin, both of Pa.

[73] Assignee: The United States of America as represented by the United States Department of Energy, Washington, D.C.

[21] Appl. No.: 647,963

[22] Filed: Jan. 30, 1991

[51] Int. Cl.$^5$ ............................................. G01N 5/04
[52] U.S. Cl. ........................................ 73/191; 55/49; 55/208; 55/270; 73/863.12
[58] Field of Search .................. 55/40, 42, 49, 50, 55, 55/189, 270, 195, 208; 73/19.1, 863.12, 19.11; 374/54

[56] References Cited

U.S. PATENT DOCUMENTS

| | | | |
|---|---|---|---|
| 2,201,870 | 5/1940 | Piercy | 55/42 |
| 2,327,111 | 8/1943 | Kimmell | 73/863.12 |
| 2,475,857 | 7/1949 | Reinert | 73/863.12 |
| 2,519,303 | 8/1950 | Whitehouse | 73/422 |
| 3,556,730 | 1/1971 | Mitacek | 23/230 |
| 3,956,921 | 5/1976 | Himes et al. | 73/863.12 |
| 4,325,247 | 4/1982 | Foss | 73/19.1 |

Primary Examiner—Bernard Nozick
Attorney, Agent, or Firm—Michael P. Hoffman; William R. Moser; Richard E. Constant

[57] ABSTRACT

An improved apparatus is provided for sampling a gaseous mixture and for measuring mixture components. The apparatus includes two sampling containers connected in series serving as a duplex sampling apparatus. The apparatus is adapted to independently determine the amounts of condensable and noncondensable gases in admixture from a single sample. More specifically, a first container includes a first port capable of selectively connecting to and disconnecting from a sample source and a second port capable of selectively connecting to and disconnecting from a second container. A second container also includes a first port capable of selectively connecting to and disconnecting from the second port of the first container and a second port capable of either selectively connecting to and disconnecting from a differential pressure source. By cooling a mixture sample in the first container, the condensable vapors form a liquid, leaving noncondensable gases either as free gases or dissolved in the liquid. The condensed liquid is heated to drive out dissolved noncondensable gases, and all the noncondensable gases are transferred to the second container. Then the first and second containers are separated from one another in order to separately determine the amount of noncondensable gases and the amount of condensable gases in the sample.

6 Claims, 2 Drawing Sheets

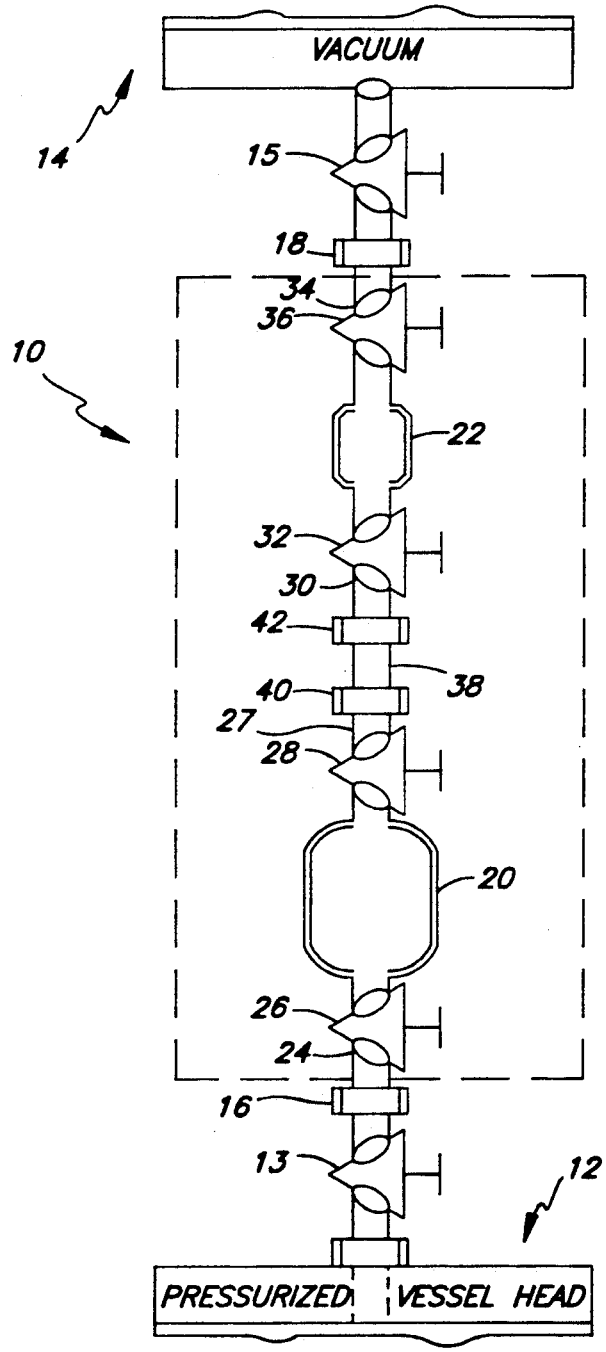
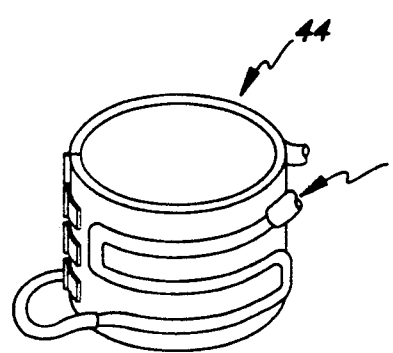
FIG. 1
FIG. 2

DUPLEX SAMPLING APPARATUS AND METHOD

GOVERNMENT CONTRACT RIGHTS

The United States Government has rights in this invention pursuant to Contract No. N-00024-79-C-4026 between the Department of the Navy and Westinghouse Electric Corporation. Pursuant to Executive Order 12344 of Feb. 1, 1982 and 42 U.S.C. 7158, title to the present invention is in the Department of Energy.

TECHNICAL FIELD OF THE INVENTION

The present invention relates to an apparatus and method for sampling fluids, and more particularly to an apparatus and method for sampling a gaseous mixture containing condensable vapors and noncondensable gases.

BACKGROUND OF THE INVENTION

Pressurized gases are used for many purposes. There are numerous vessels containing pressurized gases, and these vessels are used for a variety of purposes. More specifically, water is often used as the source of working fluid in pressurized systems. Water is generally heated to form steam which is generally contained in a closed system. Such pressurized steam systems include boilers for heating systems, steam-driven electrical generators, autoclaves, distillation apparatus, and evaporators, among others.

The working fluid in a pressurized steam system includes both condensable gases and noncondensable gases. Condensable gases include steam and water vapor. These gases will condense into liquid water when cooled by a cooling source such as cold water. The noncondensable gases are not condensed by cooling with cold water; such noncondensable gases include nitrogen and oxygen.

It is often desirable to know how much condensable gas and how much condensable gas are contained in a pressurized vessel. More specifically, in a gaseous mixture contained in a pressurized vessel, it is frequently desirable to know the ratio of condensable gases to noncondensable gases. For example, in a steam-based autoclave, it is often desirable to know the respective ratios of condensable steam and other water vapor to noncondensable gases.

To measure condensable gases, on the one hand, and noncondensable gases, on the other hand, two separate samples may be taken and two separate tests may be run. It would be desirable, however, if a single sample could be taken to enable measurement of both condensable and noncondensable gases.

Presently, there is a need for a simple and convenient apparatus for sampling the gases in a pressurized vessel, whereby the sampling apparatus is especially adapted for a determination of condensable and noncondensable gases in the gaseous sample.

SUMMARY OF THE INVENTION

Accordingly, a general object of the present invention is to provide a simple and convenient method and apparatus for sampling gases in a pressurized vessel, which is adapted for the determination of condensable and noncondensable gases in a vessel.

Another object of the invention is to provide an apparatus and method wherein one sample can be taken to enable measurement of both condensable and noncondensable gases.

Additional objects, advantages, and novel features of the invention will in part be set forth in the description that follows and will in part become apparent to those skilled in the art upon examination of the following or be learned with the practice of the invention. The above and other objects, features and advantages of the invention can be realized and attained by means of the instrumentalities and combinations particularly pointed out in the appended claims.

To achieve the foregoing and other objects, and in accordance with the purposes of the present invention as described herein, an improved apparatus is provided for sampling a gaseous mixture, whereby the apparatus is adapted to determine both the condensable and noncondensable gases in the mixture from a single sample. The apparatus includes two containers connected together in series. A first container includes two ports, with the first port being capable of selectively connecting to and disconnecting from a sample source and the second port being capable of selectively connecting to and disconnecting from a second container.

A second container also includes two ports, with a first port being capable of selectively connecting to and disconnecting from the second port of the first container and a second port being capable of selectively connecting to and disconnecting from a differential pressure source. The second port of the first container and the first port of the second container are connected to an expansion conduit located therebetween. In the presently preferred embodiment, the expansion conduit is sufficiently transparent to allow visualization of the liquid level therein.

Since the apparatus of the invention includes two sampling containers connected in series, it can be regarded as a duplex sampling apparatus. A method of employing the duplex sampling apparatus is also described and claimed herein.

When the apparatus of the invention is employed, the duplex sampling apparatus is first evacuated. Heat can be applied to the apparatus during evacuation to strip out residual gases that may be present in the apparatus. The first container is then sealed with respect to the second container. Next, a sample of a gaseous mixture enters the first container of the duplex sampling apparatus from the pressurized vessel. As the sample of gaseous mixture enters the first container, the first container is cooled, so that the condensable gases inside the first container form a liquid condensate. Condensation of condensable gases in the first container proceeds until the first container is filled with liquid. The first container is then sealed with respect to the pressurized system.

At this stage, the first container is liquid-filled, except for the possible presence of a bubble of noncondensable gases that are compressed under the system pressure near the sealed second port of the first container. At a high system pressure, the cooled condensate in the first container will contain a significant amount of noncondensable gases.

The seal between the first and second containers is removed, and the compressed bubble from the first container is permitted to expand into the second container. The first container is then heated to drive out dissolved noncondensable gases from the liquid. As the first container is heated, the liquid condensate therein expands into the expansion conduit. When the expanded condensate reaches the first port of the second container, the second container is sealed by closing this port, whereby the noncondensable gases are trapped within the second container. If, in heating the condensate to drive out the non-condensable gases, the heated condensate expands beyond the expansion conduit into the second container, the second container is then sealed during cooling of the condensate by closing this port when the contracting condensate recedes to the bottom of the second container.

The thusly-heated liquid is then permitted to cool and, in doing so, the liquid contracts and recedes from the expansion conduit, returning to the first container which is sealed by closing its upper port. In this manner, the second container now contains the noncondensable gases from a single sample, while the first container contains the liquid condensate resulting from condensation of the condensable gases in the same sample.

Next, the first and second containers are separated from one another and the mass increases due to the presence of condensate from condensable gases in the first container and the presence of noncondensable gases in the second container are each determined. The sum of both increases represents the total of noncondensable and condensable gases in the single sample from the pressure source.

While the volume of the first container is generally sufficiently large to permit satisfactory condensable gases determination by simply weighing the container and its now liquified condensable gases or condensate, the sample collected in the second container is relatively small compared to the weight of the container (by several orders of magnitude) so that the weight of gas in the second container cannot be accurately determined using commonly available laboratory balances. Accordingly, in the presently preferred embodiment of this invention the second container is connected to a sensitive pressure measuring device and the mass of the gas therein calculated from the container volume and gas temperature and pressure according to the ideal gas law: $PV = nRT$ wherein n is the total mass of the gas in mols. Analysis of the stripped noncondensable gas yields the volume and thus the molar mass $n_i$ of each constituent i of the noncondensable gas, such that $n = \Sigma n_i$.

An elegantly simple and presently preferred method for determining the weight of condensate liquid in the first container involves the use of a transparent expansion pipe described hereinafter. The condensate liquid left in the first container after stripping out the noncondensable gas is at a moderate pressure, and pressure variations commonly encountered in actual practice do not significantly affect the density of the condensate liquid at ambient temperatures. The condensate in the first container is expanded by heating to strip out the noncondensable gases into the second container, driving the condensate into the transparent expansion pipe. As the heated condensate slowly cools down, its level recedes downward into the first container. One can determine the temperature of the first container when the condensate level first recedes downward and out of view in the expansion pipe; at that point, the liquid condensate just fills the known volume of the first container.

The density of the condensate can be conveniently interpolated from tables giving density as a function of temperature, and the simple product of such density value and the volume of the first container (which is known as a function of temperature) gives the mass of condensate in the first container.

From the sum figure and the individual figures for noncondensable and condensable gases that are determined separately, weight ratios of the respective components in the original single sample can be determined. For example, for the original sample, the weight ratio of condensable gases to the total sample is obtained by dividing the weight of condensable gases by the total weight of both condensable and noncondensable gases. The weight ratio of noncondensable gases in the original sample is obtained by dividing the weight of noncondensable gases by the total weight of both condensable and noncondensable gases. The weight ratio of the condensable gases to the noncondensable gases in the original sample is obtained by dividing a) the weight of the condensable gases contained in the first container by b) the weight of the noncondensable gases in the second container.

Still other objects of the present invention will become readily apparent to those skilled in his art from the following description, wherein there is shown and described a preferred embodiment of this invention. Simply by way of illustration, the invention will be set forth in part in the description that follows and in part will become apparent to those skilled in the art upon examination of the following or may be learned with the practice of the invention. Accordingly, the drawings and descriptions will be regarded as illustrative in nature and not as restrictive.

BRIEF DESCRIPTION OF THE DRAWINGS

The accompanying drawings, incorporated in and forming a part of the specification, illustrate several aspects of the present invention and, together with the written description, serve to further explain the principles of the invention.

FIG. 1 shows an embodiment of the duplex sampling apparatus of the invention in partial cross-section.

FIG. 2 shows a cooling and/or heating jacket for placement around the first container in the duplex arrangement of sampling containers.

DETAILED DESCRIPTION

Figure 3:
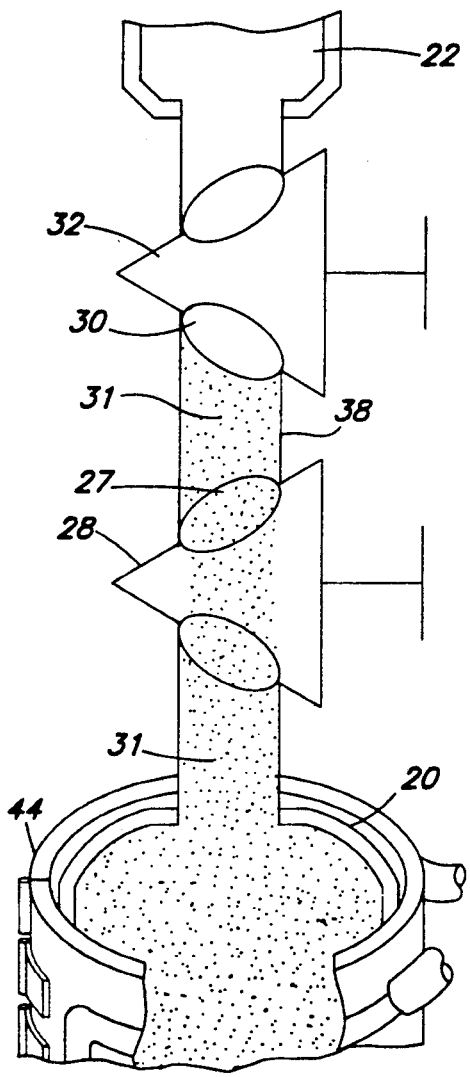
FIG. 3 is an enlarged view of a transparent expansion pipe which is placed between the first and second sampling containers shown in FIG. 1; the column of liquid in the expansion pipe is shown at the first port of the second sampling container.

Referring to the drawings, FIG. 1 shows a presently preferred embodiment of the duplex sampling apparatus 10 of the present invention. The duplex sampling apparatus 10 is located between a pressurized vessel 12 and a source 14 of vacuum. The pressurized vessel 12 includes a valve 13, and the duplex sampling apparatus 10 is connected to the valve 13 by means of standard pipe connection 16. Similarly, the vacuum source 14 includes a valve 15, and the duplex sampling apparatus 10 is connected to valve 15 by means of standard pipe connection 18. Alternatively, a quick-disconnect union can be used in place of either or both of connections 16 or 18.

The embodiment of the duplex sampling apparatus 10 of the invention shown in FIG. 1 includes a first sampling container 20 and a second sampling container 22. The first sampling container 20 includes a first port 24 which is selectively opened and closed by first port valve 26. The first sampling container 20 also includes a second port 27 which is selectively opened and closed by a second port valve 28.

The second sampling container 22 includes a first port 30 which is selectively opened and closed by first port valve 32. The second sampling container 22 also includes a second port 34 which is selectively opened and closed by second port valve 36.

An expansion conduit 38, preferably transparent, is located between the second port valve 28 of the first sampling container 20 and the first port valve 32 of the second sampling container 22. Standard pipe couplers 40 and 42 are used to connect the expansion conduit 38 to the second port valve 28 of the first sampling container 20 and to the first port valve 32 of the second sampling container 22, respectively.

In FIG. 2, a combined heating and cooling jacket 44 is shown. Combined heating and cooling jacket 44 can be placed around the first sampling container 20 (shown in FIG. 1) to provide heating and cooling as needed. The combined heating and cooling jacket 44 can employ a circulating heat transfer medium, such as water or glycol-based media. Alternatively, the combined heating and cooling jacket 44 can be electrically powered which heats by ohmic resistance and cools by the Peltier effect.

A method of employing the duplex sampling apparatus 10 of the invention shown in FIG. 1 is now described. When the duplex sampling apparatus 10 is employed, the apparatus is first evacuated by being connected with vacuum source 14.

If the evacuation step is conducted when the duplex sampling apparatus 10 is not connected to the pressurized vessel 12, the first port valve 26 of the first sampling container 20 would be closed; and second port valve 28 of the first sampling container 20 would be open as would the first port valve 32 and the second port valve 36 of the second sampling container 22. If the duplex sampling apparatus 10 is evacuated while it is not connected to the pressurized vessel 12, prior to being installed on the pressurized vessel 12, it is necessary to open valve 13 a short time before carrying out the sampling from the pressurized vessel 12. This time interval permits the small amount of air trapped in pipe connection 16 to dissipate into the vapor space of the pressurized vessel 12.

However, if the evacuation step is conducted when the duplex sampling apparatus 10 is connected to the pressurized vessel 12, as shown in FIG. 1, then first port valve 26 of the first sampling container 20 would be open, and the valve 13 of the pressurized vessel 12 would be closed.

Heat can be applied to the apparatus during evacuation to strip out residual gases which may be present in the apparatus. After evacuation, the second port valve 36 of the second sampling container 22 is closed, and the first sampling container 20 is sealed with respect to the second sampling container 22 by closing second port valve 28 of the first sampling container 20. Then the valve 13 is opened, and a sample of a gaseous mixture from the pressurized vessel 12 enters the first sampling container 20 of the duplex sampling apparatus.

For purposes of illustration the pressurized vessel 12 contains steam, such as present in an autoclave (not shown). As the gaseous mixture enters the first sampling container 20, the first sampling container 20 is cooled by jacket 44 (brought to approximately 65° F.), whereby the steam condenses into liquid water inside the first sampling container 20. Condensation of steam in the first sampling container 20 proceeds until the first sampling container 20 is filled with liquid. Then the first sampling container 20 is sealed with respect to the pressurized vessel 12 by closing first port valve 26 of the first sampling container 20 and by closing valve 13.

At this stage, the first sampling container 20 is liquid-filled, except for the possible presence of a bubble of noncondensable gases that are compressed under the autoclave system pressure near the sealed second port of the first sampling container 20. At a high system pressure, the cooled condensate in the first sampling container 20 generally also contains a significant amount of noncondensable gases that are not present in the bubble under system pressure.

Next the seal between the first and second sampling containers is removed by opening second port valve 28 and first port valve 32, and the compressed bubble from the first sampling container 20 is permitted to expand into the second sampling container 22.

As shown in FIG. 3, the first sampling container 20 is then heated by jacket 44 (now brought to approximately 200° F.) to drive out dissolved noncondensable gases from the condensed liquid 31, shown in the drawing as a pattern of dots. Non-condensable gas solubility in water is at a minimum at a temperature of about 200° F. As the first sampling container 20 is heated, the liquid condensate expands up from the first sampling container 20 into the expansion conduit 38.

As shown in FIG. 3, the expanded condensate reaches the first port 30 of the second sampling container 22. At this stage, the second sampling container 22 is sealed by closing first port valve 32, whereby the noncondensable gases are trapped within the second sampling container 22.

Figure 4:
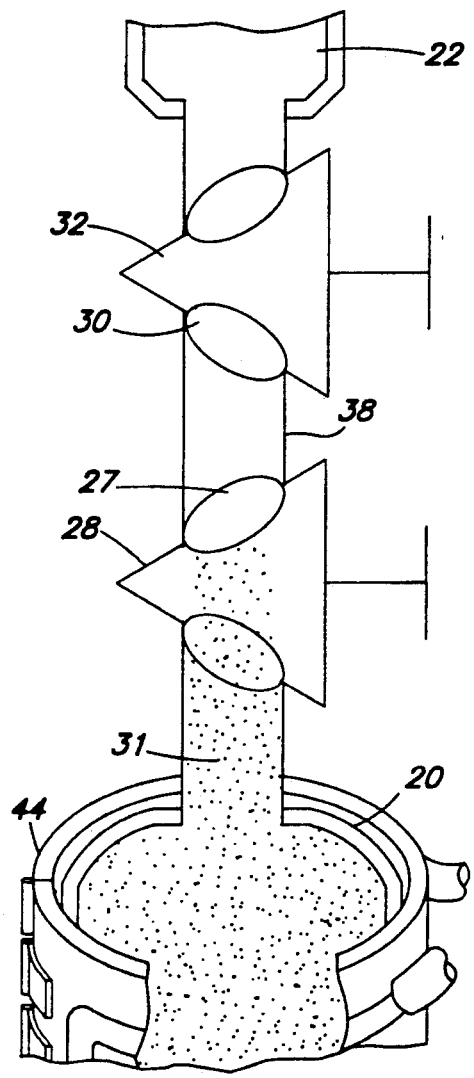
FIG. 4 is an enlarged view of the transparent expansion pipe shown in FIG. 3 wherein the column of liquid is shown just below the valve controlling the second port in the first sampling container.

The heated liquid 31 is then permitted to cool. In doing so, the liquid 31 contracts and recedes from the expansion conduit 38, returning to the first sampling container 20 as shown in FIG. 4 where condensed liquid 31 is just below second port valve 28.

Since the second sampling container 22 contains the noncondensable gases, and the first sampling container 20 contains the liquid condensate 31 resulting from condensation of steam (a condensable gas), the first and second sampling containers 20 and 22 are separated from one another and the respective mass increases due to the presence of noncondensable gases in the second sampling container 22 and liquid condensate from condensable steam in the first sampling container 20 are determined. The sum of both mass increases represents the total of noncondensable and condensable gases. From the sum figure and the individual figures for noncondensable and condensable gases, ratios can be determined. In practice, the ratio of noncondensable gas to condensable gas is conveniently expressed in units of cc/kg as the volume (in cubic centimeters) of noncondensable gas at standard temperature and pressure per kilogram of condensate.

As described above, with the invention, an apparatus and method for sampling gases in a pressurized vessel are provided which are adapted for separating condensable from noncondensable gases so that a determination of condensable and noncondensable gases in the vessel can be made. Also, with the invention, an apparatus and method are provided wherein only one sample need be taken to enable measurement of both condensable and noncondensable gases.

The foregoing description of the invention has been presented for purposes of illustration and description. It is not intended to be exhaustive or to limit the invention to the precise form disclosed. Obvious modifications or variations are possible in light of the above teachings. For example, it may not be necessary to provide a cooling jacket for the first sampling container 20. If the uncooled first sampling container 20 is of sufficient mass and at low enough temperature such that its mass provides an adequate heat sink, there may be no need to cool the first sampling container 20 in order to condense vapor which enters it.

All components in the duplex sampling apparatus of the invention have a pressure rating sufficient to withstand the pressure of the system that is being sampled. The sizes of the components of the duplex sampling apparatus can be varied, depending upon the specific requirements of a given application.

The presently preferred embodiment described herein illustrates the principles of the invention and its practical application so that one of ordinary skill in the art can utilize the invention in various embodiments and with various modifications as are suited to the particular use contemplated. It is intended that the scope of the invention be defined by the claims appended hereto.

We claim:

1. A container assembly sampling apparatus for separating noncondensable gases and condensable vapors from an upstream vapor-gas mixture, comprising:

a first container assembly which includes a first container and two ports and valves, a first port and valve capable of selectively connecting contents of said first container to and disconnecting contents of said first container from a sample source containing said vapor-gas mixture and a second port and valve capable of selectively connecting contents of said first container to and disconnecting contents of said first container from a downstream expansion conduit and further including means for cooling said first container, an expansion conduit downstream of said first container assembly capable of communicating with the contents of said first container through said second port and valve of said first container, a second container assembly downstream of said expansion conduit which includes a second container and two ports and valves, a first port and valve capable of selectively connecting contents of said second container to and disconnecting contents of said second container from said expansion conduit, and a second port and valve capable of selectively connecting contents of said second container to and disconnecting contents of said second container from a downstream differential pressure source, and means in said expansion conduit for disassembly of the container assemblies, whereby the weights of the condensable vapors and noncondensable gases can be determined.

2. The apparatus described in claim 1, further including means for heating said first container.

3. The apparatus as defined in claim 1, wherein said expansion conduit is transparent.

4. The apparatus as defined in claim 1, including a differential pressure vacuum source.

5. A method of measuring the condensable vapor content and the noncondensable gaseous content of a mixture of condensable vapors and noncondensable gases, comprising the steps of:

collecting a quantity of a mixture of condensable vapors and noncondensable gases in a first container, cooling the first container whereby the condensable vapors in the mixture are condensed to form a condensate and retained in the first container, transferring the noncondensable gases from the first container to a downstream second container, wherein said transferring is accomplished by sealing off said noncondensable gases in said second container as soon as the interface of said condensed liquid and said noncondensable gases is at said first port of said second container, determining the quantity of condensable vapors retained in the first container by weighing said first container, including the condensate in said first container, and measuring the pressure of noncondensable gases in said second container, measuring the temperature of noncondensable gases in said second container, thereby determining the quantity of noncondensable gases in the second container from the temperature, pressure and volume, using the ideal gas law: $P_v = nRT$, whereby the ratio of condensable vapors to noncondensable gases in the mixture is determined.

6. A method of measuring the condensable vapor content and the noncondensable gaseous content of a mixture of condensable vapors and noncondensable gases, comprising the steps of:

collecting a quantity of a mixture of condensable vapors and noncondensable gases in a first container, cooling the first container whereby the condensable vapors in the mixture are condensed to a liquid and retained in the first container, heating the liquid in the first container to drive out dissolved noncondensable gases from the liquid, transferring the noncondensable gases from the first container to a downstream second container, wherein said transferring is accomplished by sealing off said noncondensable gases in said second container as soon as the interface of said noncondensable gases is at said first port of said second container, determining the quantity of condensable vapors retained in the first container by weighing said first container, including the condensate, and measuring the pressure of noncondensable gases in said second container, measuring the temperature of noncondensable gases in said second container, thereby determining the quantity of noncondensable vapors in the second container from the temperature, pressure and volume, using the ideal gas low: $P_v = nRT$, whereby the ratio of condensable vapors to noncondensable gases in the mixture is determined.

* * * * *